United States Patent
Zheng et al.

(10) Patent No.: US 7,941,203 B2
(45) Date of Patent: May 10, 2011

(54) MULTIMODALITY IMAGING SYSTEM

(75) Inventors: Quanlu Zheng, Shenyang (CN); Tie Gao, Shenyang (CN); Jiadi Li, Shenyang (CN); Kai Liu, Shenyang (CN); Qingze Yu, Shenyang (CN); Baowei Xu, Shenyang (CN); Haitao Mu, Shenyang (CN); Qizhi Zhang, Shenyang (CN); Xinghua Zhao, Shenyang (CN)

(73) Assignee: Neusolft Positron Medical Systems Co., Ltd., Shenyang (CN)

( * ) Notice: Subject to any disclaimer, the term of this patent is extended or adjusted under 35 U.S.C. 154(b) by 900 days.

(21) Appl. No.: 11/903,324

(22) Filed: Sep. 21, 2007

(65) Prior Publication Data

US 2008/0081985 A1    Apr. 3, 2008

(30) Foreign Application Priority Data

Sep. 30, 2006   (CN) .......................... 2006 1 0140110

(51) Int. Cl.
*A61B 5/05*   (2006.01)
(52) U.S. Cl. ........................................... 600/407; 5/630
(58) Field of Classification Search .................. 600/407, 600/411, 415, 427, 436; 5/630, 632–635, 5/601
See application file for complete search history.

(56) References Cited

U.S. PATENT DOCUMENTS

| | | | |
|---|---|---|---|
| 6,490,476 B1 | 12/2002 | Townsend et al. | |
| 6,631,284 B2 | 10/2003 | Nutt et al. | |
| 6,754,519 B1 | 6/2004 | Hefetz et al. | |
| 6,754,520 B2 | 6/2004 | DeSilets et al. | |
| 6,885,165 B2 | 4/2005 | Henley et al. | |
| 6,961,606 B2 | 11/2005 | DeSilets et al. | |
| 7,613,492 B2 * | 11/2009 | Altman et al. | 600/407 |
| 2003/0078488 A1 | 4/2003 | DeSilets et al. | |
| 2004/0030246 A1 | 2/2004 | Townsend et al. | |
| 2005/0023471 A1 * | 2/2005 | Wang et al. | 250/363.04 |

* cited by examiner

*Primary Examiner* — Brian Casler
*Assistant Examiner* — Parikha S Mehta
(74) *Attorney, Agent, or Firm* — Kinney & Lange, P.A.

(57) ABSTRACT

A multimodality imaging system, comprising: a first imaging system for forming a first image; a second imaging system for forming a second image; and a rotating device on which the first imaging system and the second imaging system are fixed so that the first imaging system and the second imaging system are selectively rotated to a scanning position.

10 Claims, 5 Drawing Sheets

Rotating base is at 0° position and CT scanning plane is adjacent to patient.

PET scanning plane is adjacent to patient after rotating base is rotated through 180°

Fig.1

Rotating base is at 0° position and CT scanning plane is adjacent to patient.

PET scanning plane is adjacent to patient after rotating base is rotated through 180°

Fig.2a

Rotating base is at 0° position and CT scanning plane is adjacent to patient.

PET scanning plane is adjacent to patient after rotating base is rotated through 180°

MULTIMODALITY IMAGING SYSTEM

BACKGROUND

1. Field of the Invention

The present invention relates to a medical apparatus, and particularly to a multimodality imaging system.

2. Description of the Related Art

Figure 1:
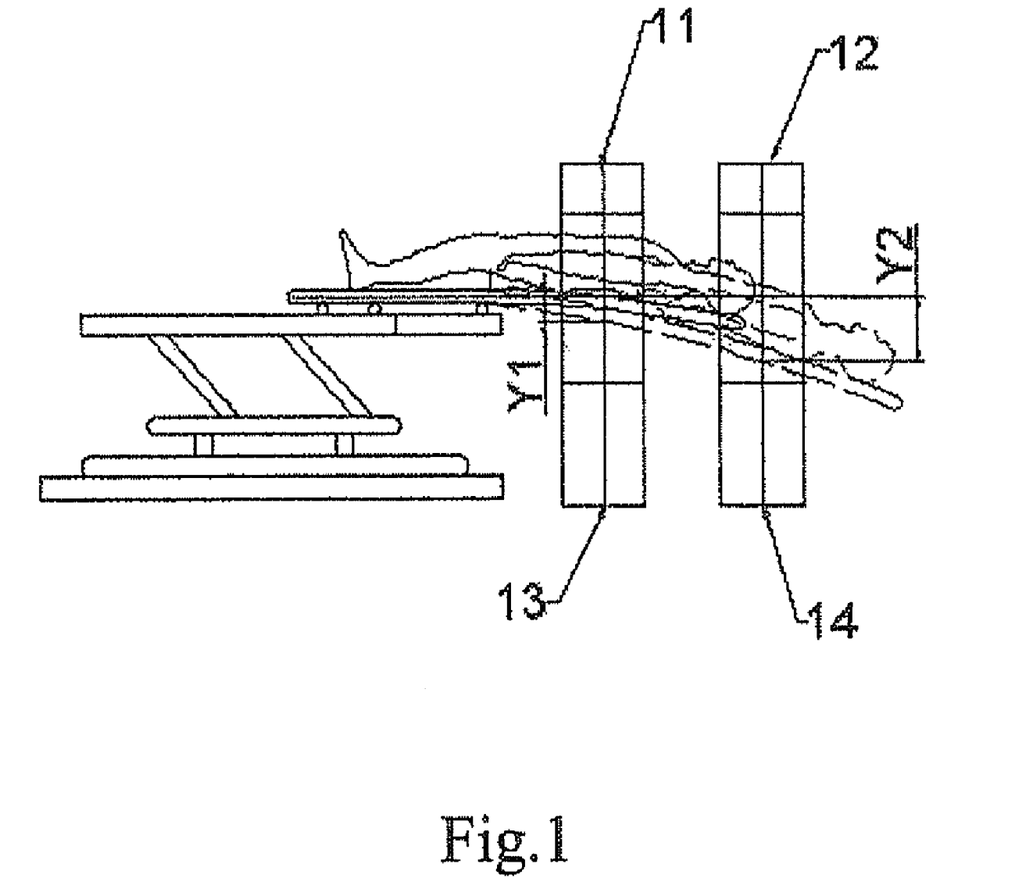
FIG. 1 is a schematic view showing difference of deformation extent of a bed pallet due to difference of lengths that the bed pallet extends.

When using a multimodality imaging system including medical apparatuses such as a CT (Computerized Tomography) apparatus, a MRI (Magnetic Resonance Imaging) apparatus, a PET (Positron Emission Tomography) apparatus, a SPECT (Single Photon Emission Computed Tomography) apparatus, in order to assure the effectiveness of synthesis of images formed by different apparatuses, it must be assured that an extent of deformation of a bed pallet is uniform at different detector positions when a patient on the bed pallet is scanned in the multimodality imaging system. Only when the extent of deformation is uniform, could it be assured that the image fusion is correct and positive to the effect of the diagnoses. When a patient is scanned with a PET apparatus 11 and a CT apparatus 12, an extent of deformation of a bed pallet is not uniform due to different lengths that the bed pallet extends at a PET scanning plane 13 and a CT scanning plane 14, that is, Y1 is not equal to Y2, as shown in FIG. 1. As a result, it cannot be assured that the image fusion is correct, thus degrading the effect of the diagnoses on the patient.

SUMMARY

It is an object of the present invention to provide a multimodality imaging system capable of assuring that a moving trajectory of a patient is uniform when the patient is scanned at different subsystems and that positions of the subsystems remain constant before and after maintenance of apparatuses of the system.

In accordance with one aspect of the present invention, there is provided a multimodality imaging system comprising a first imaging system for forming a first image; a second imaging system for forming a second image; and a rotating device on which the first imaging system and the second imaging system are fixed so that the first imaging system and the second imaging system are selectively rotated to a scanning position.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION

Figure 2A:
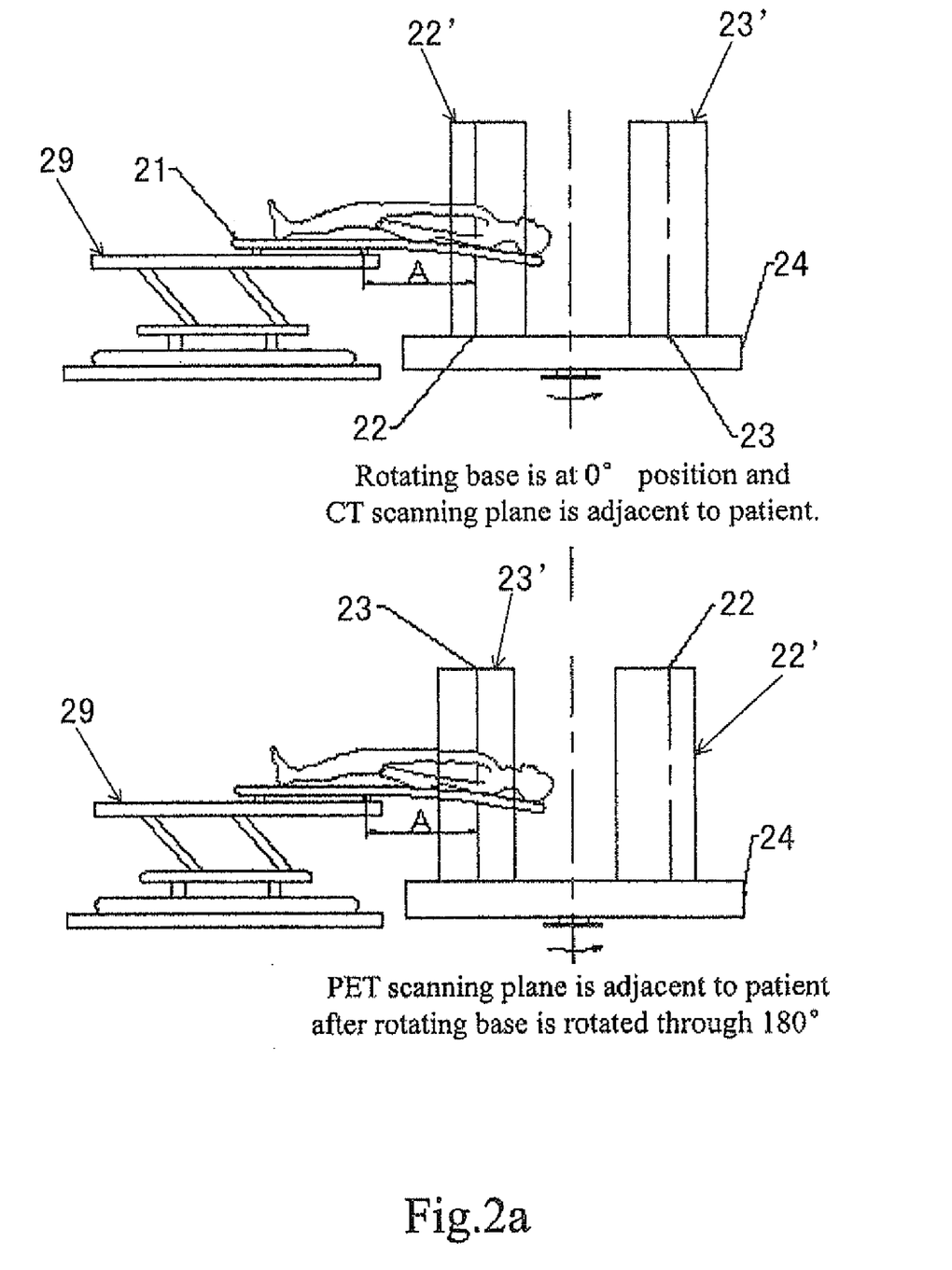
FIG. 2a is a schematic view showing operating principle of PET/CT equipment with a rotating base in a state that a bed frame is stationarily fixed on a floor surface while the PET/CT equipment is mounted on the rotating base.

A multimodality imaging system according to an embodiment of the present invention comprises a first imaging system CT 22' (having a scanning plane 22) and a second imaging system PET 23' (having a scanning plane 23) mounted on a rotating base 24 according to the present invention, and a bed 29 with a bed body mounted on a floor surface as shown in FIG. 2a. The first imaging system CT 22' (having the scanning plane 22) is positioned adjacent to a patient, and the second imaging system PET 23' (having the scanning plane 23) is positioned away from the patient. When the first imaging system CT 22' (having the scanning plane 22) begins to scan the patient, a bed pallet 21 extends a length of A. After the first imaging system CT 22' (having the scanning plane 22) has scanned the patient, the rotating base 24 is rotated by or through 180° in a certain direction, so that the second imaging system PET 23' (having the scanning plane 23) is positioned adjacent to the patient. The first imaging system CT 22' (having the scanning plane 22) and the second imaging system PET 23' (having the scanning plane 23) are mounted at an appropriate position on the rotating base 24 by accurately calculating positional relationship between the first imaging system CT 22' (having the scanning plane 22) and the second imaging system PET 23' (having the scanning plane 23). As a result, it can be assured that the bed pallet 21 still extends the length of A when the second imaging system PET 23' (having the scanning plane 23) begins to scan the patient. Therefore, it can be assured that deformation of the bed pallet 21 is uniform in both the first imaging system CT 22' (having the scanning plane 22) and the second imaging system PET 23' (having the scanning plane 23).

Figure 2B:
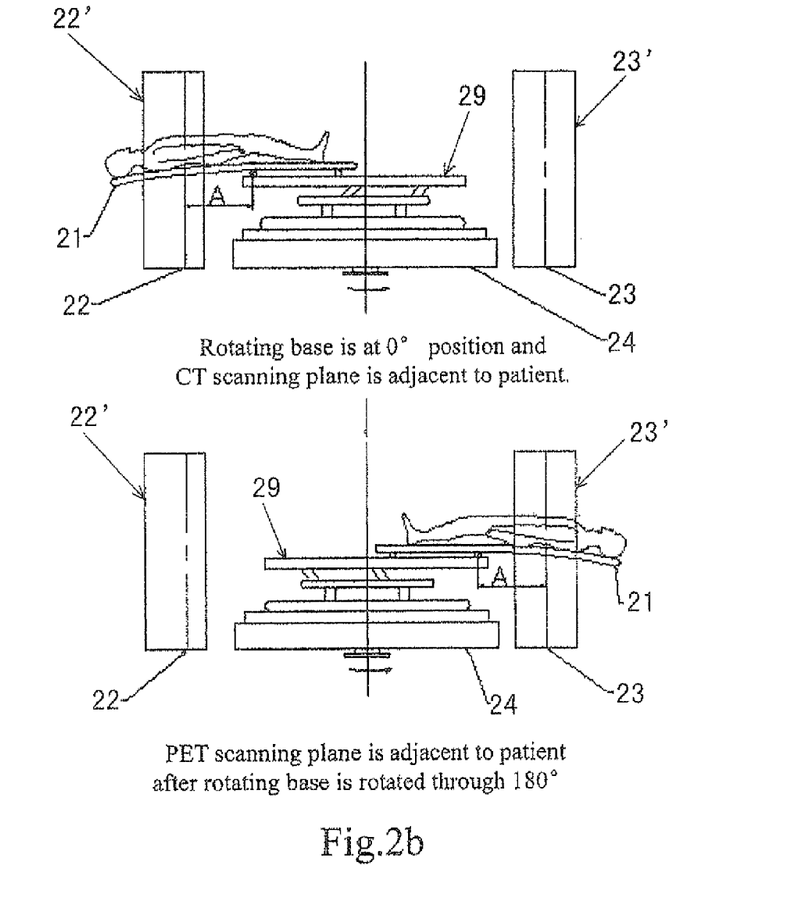
FIG. 2b is a schematic view showing operating principle of PET/CT equipment with a rotating base in a state that the PET/CT equipment is stationarily fixed on a floor surface while a bed frame is mounted on the rotating base.
Figure 3A:
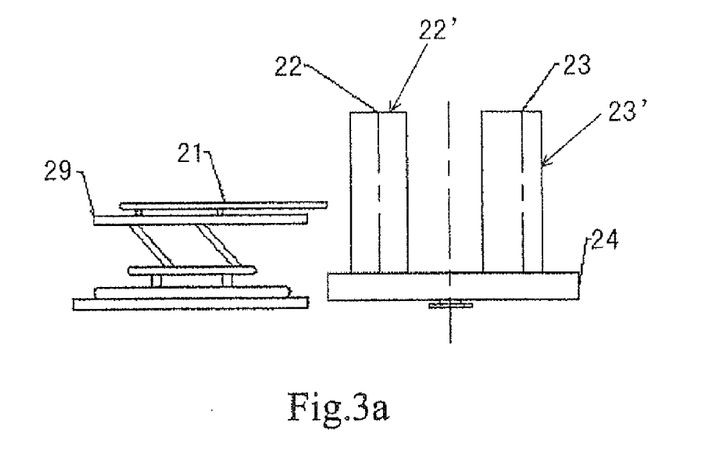
FIG. 3a is a schematic view showing components of a multimodality imaging system in which a bed frame is stationarily fixed on a floor surface while PET/CT equipment is mounted on a rotating base.
Figure 3B:
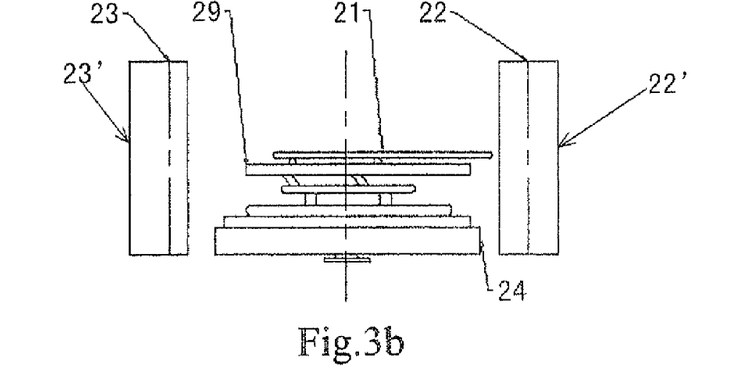
FIG. 3b is a schematic view showing components of a multimodality imaging system in which PET/CT equipment is stationarily fixed on a floor surface while a bed frame is mounted on a rotating base.

A multimodality imaging system according to another embodiment of the present invention comprises a first imaging system CT 22' (having a scanning plane 22) and a second imaging system PET 23' (having a scanning plane 23) mounted on a floor surface on both sides of a rotating base 24 according to the present invention, as shown in FIG. 2b. The scanning planes 22, 23 of the first imaging system CT 22' and the second imaging system PET 23' are parallel to each other and symmetrical with respect to an axis of the rotating base. In addition, the multimodality imaging system further comprises a bed 29 with a bed body. The bed 29 is mounted on the rotating base 24. The first imaging system CT 22' (having the scanning plane 22) is positioned adjacent to a patient, and the second imaging system PET 23' (having the scanning plane 23) is positioned away from the patient. When the first imaging system CT 22' (having the scanning plane 22) begins to scan the patient, the bed pallet 21 extends a length of A. After the first imaging system CT 22' (having the scanning plane 22) has scanned the patient, the rotating base 24 is rotated by 180° in a certain direction, so that the second imaging system PET 23' (having the scanning plane 23) is positioned adjacent to the patient. The first imaging system CT 22' (having the scanning plane 22) and the second imaging system PET 23' (having the scanning plane 23) are mounted at an appropriate position on the floor surface on both sides of the rotating base 24 by calculating positional relationship between the first imaging system CT 22' (having the scanning plane 22) and the second imaging system PET 23' (having the scanning plane 23) with accuracy. As a result, it can be assured that the bed pallet 21 still extends the length of A when the second imaging system PET 23' (having the scanning plane 23) begins to scan the patient. Therefore, it can be assured that deformation of the bed pallet 21 is uniform in both the first imaging system CT 22' (having the scanning plane 22) and the second imaging system PET 23' (having the scanning plane 23).

In some alternative embodiments, a movable patient table, a movable holder, or a movable patient supporting device is used instead of the bed.

Figure 4:
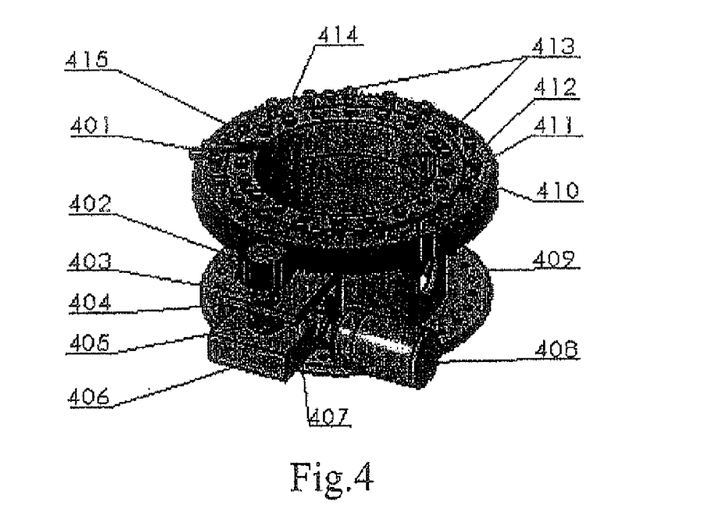
FIG. 4 is a schematic view showing a rotation mechanism of a base.
Figure 5:
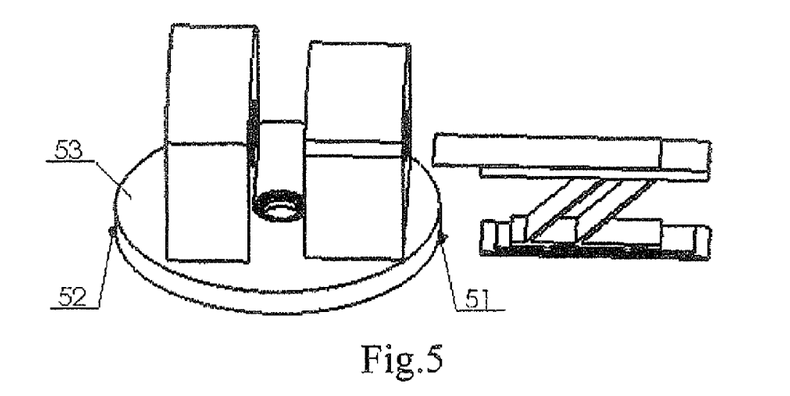
FIG. 5 is a schematic view showing positions at which two mechanical positioning sleeve parts are assembled.
Figure 6:
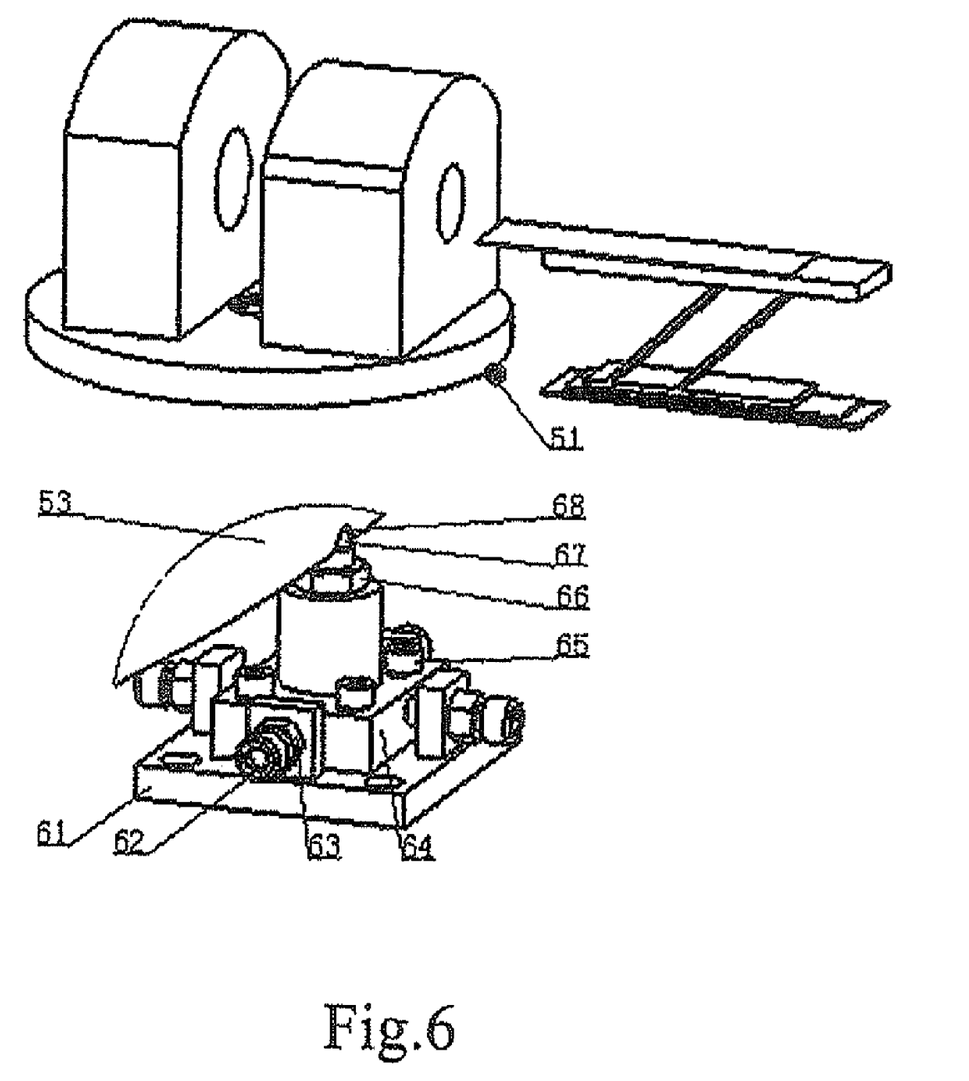
FIG. 6 is a schematic view showing the mechanical positioning sleeve parts of FIG. 5.

The rotatable base may be adjustable and comprises: a base disk 53 as shown in FIG. 5, an external gear type rotary bearing (including a rotary bearing inner ring 414 and an outer ring 412), a pinion 402, a shaft 403, a coupling 405, a worm-gear speed reducer 406 (or a bevel-gear speed reducer or other reducer), a motor 408 with a brake, a support 407, and a base disk stand 409. The base disk 53 shown in FIG. 5 is coupled with the outer ring 412 of the external gear type rotary bearing by bolts 411 and positioning pins 413 shown in FIG. 4. The inner ring 414 of the external gear type rotary bearing is coupled with the base disk stand 409 by bolts 411 and positioning pins 413 shown in FIG. 4. The support 407 is used to hold the worm-gear speed reducer 406, the pinion 402, the shaft 403, and the coupling 405. The motor 408 with the brake is coupled with a flange of a housing of the worm-gear speed reducer 406 by bolts, and the support 407 is connected to the base disk stand 409 by welding or bolts. The pinion 402 meshes with an external gear on the outer ring 412 of the external gear type rotary bearing as shown in FIG. 4, so that the motor with the brake rotates the base disk 53 by the worm-gear speed reducer 406, the pinion 402 and the external gear on the outer ring 412 of the external gear type rotary bearing (including a rotary bearing inner ring 414 and a outer ring 412). A capacitive proximity switch support 401 is fixed at an appropriate position on an upper surface of the outer ring 412 of the external gear type rotary bearing, and a capacitive proximity switch 415 is fixed at an appropriate position on the capacitive proximity switch support 401. An inclined metal block 410 is fixed at an appropriate position on the inner ring 412. The capacitive proximity switch 415 is a position sensor capable of outputting a value indicative of the opening/closing degree or extent thereof. A measuring probe of the capacitive proximity switch 415 usually is a plate of a capacitor, while the other plate of the capacitor is an object itself. When the object is approaching the proximity switch, a dielectric constant between the object and the proximity switch is changed, so that a state of an electric circuit connected with the measuring probe is accordingly changed. As a result, the proximity switch is controlled to be turned on and off. An encoder 404 shown in FIG. 4 is connected to an end of a worm of the worm-gear speed reducer 406. When the base disk 53 rotates by or through about 160°, the capacitive proximity switch 415 approaches the inclined metal block 410 shown in FIG. 4. The dielectric constant of the capacitive proximity switch 415 is changed, so that the state of the electric circuit connected with the measuring probe is accordingly changed. The capacitive proximity switch 415 sends a control signal to control the motor 408 to be decelerated together with the encoder 404. When the base disk is rotated by or through 180°, the capacitive proximity switch 415 sends control signal to control the motor 408 to be braked and stopped. Since the two-stage speed reducing system having the worm-gear speed reducer 406 with a speed reducing ratio of about 40 and the pinion-outer gear reducer with a speed reducing ratio of about 6 is selected, the base disk 53 shown in FIG. 5 rotates at a speed of about 6 rpm before the capacitive proximity switch sends the control signal to instruct the motor with the brake to be decelerated. In the operating condition that the rotating speed of the base disk is not high, as shown in FIG. 5, two ball head plunger type positioning post sleeve parts 51 and 52, positions of which can be adjusted with accuracy, are mounted at appropriate positions on a floor surface perpendicular to an edge of the base disk 53, respectively, and are positioned at 180° with respect to each other. Each of the positioning post sleeve parts 51 and 52 comprises an anchor plate 61 shown in FIG. 6. When the system is mounted, the anchor plate 61 is firmly connected to the floor surface by anchor bolts or expansion bolts, and is fixed with the floor surface by pouring concrete around the anchor plate 61, so that it is assured that the anchor plates 61 of the positioning post sleeve parts 51 and 52 are firmly connected with the floor surface. When the positioning post sleeve parts 51 and 52 are mounted and adjusted, four finely adjusting bolts 62 on each of the anchor plates 61 of the positioning post sleeve parts 51 and 52, and a finely adjusting nut 66 on a top of each of the positioning post sleeve parts 51 and 52 are finely adjusted, so that a ball 67 of a ball head plunger type positioning post 64 of each of the ball head plunger type positioning post sleeve parts 51 and 52 is just fitted in a stopping point recess 68 formed in the edge of the base disk 53. Then, nuts 63 and bolts 65 of each of the ball head plunger type positioning post sleeve parts 51 and 52 are screwed down (see FIG. 6). As a result, when the motor 408 with the brake (shown in FIG. 4) is stopped, the base disk 53 can be positioned with accuracy. The base disk 53 is adapted to fix a plurality of imaging apparatuses. The base disk stand is adapted to bear the load of the plurality of imaging apparatuses so that the overall load of the plurality of imaging apparatuses is distributed uniformly. The adjustable rotating base can provide the plurality of imaging apparatuses with the different rotating angles.

The present invention effectively solves the inconsistence of deformation of the bed pallet in at least two imaging systems during scanning a patient by the rotating base and at the same time brings about a prominent advantage that there is no requirement for addition of length of the bed pallet during scanning a patient since the multimodality imaging system adopts the rotating base. As a result, the bed pallet can fulfill a requirement of the multimodality imaging system no matter which one of a first imaging system and a second system is used. It is thus possible for a medical establishment that has a first imaging system to constitute a multimodality imaging system by buying a second imaging system required, so that the medical establishment can greatly save cost for buying equipment. On the other hand, positions of the two imaging systems are fixed independently of each other by separately assembling the first imaging system and second imaging system on the rotating base with a distance therebetween which is enough for maintenance. No imaging system is required to be moved in maintenance, so that there is no need of realignment before and after the maintenance. Therefore, the present invention effectively solves a problem of maintenance of the multimodality imaging system.

Operating processes of the multimodality imaging system according to the present invention are described as follows.

EXAMPLE 1

When a patient is to be scanned by the first imaging system CT 22' as shown in FIG. 2a, the bed pallet 21 is located at an original position, the first imaging system CT 22' is positioned adjacent to the bed pallet 21, and the second imaging system PET 23' is positioned away from the bed pallet 21. The bed pallet 21 is moved forward so that the patient is sent to the scanning plane 22 of the first imaging system CT 22'. Firstly, the patient is scanned by the first imaging system CT 22'. After the patient has been scanned by the first imaging system CT 22', the bed pallet 21 is moved back to the original position from a scanning position. Then, the first imaging system CT 22' and the second imaging system PET 23' rotate by or through 180° by an automatic control device, so that the second imaging system PET 23' is positioned adjacent to the bed pallet 21 and the first imaging system CT 22' is positioned away from the bed pallet 21. The bed pallet 21 is moved forward so that the patient is sent to the scanning plane 23 of the second imaging system PET 23'. Then, the patient is scanned by the second imaging system PET 23'. After the patient has been scanned by the second imaging system PET 23', the bed pallet 21 is moved back to the original position. The scanning process is completed. Finally, the first imaging system CT 22' and the second imaging system PET 23' reversely rotate by or through 180° by the automatic control device, so that the first imaging system CT 22' and the second imaging system PET 23' are resumed to original positions thereof. In addition, the first imaging system CT 22' and the second imaging system PET 23' can maintain their respective full function abilities of clinic applications independently.

EXAMPLE 2

When a patient is to be scanned by the first imaging system CT 22' as shown in FIG. 2b, the bed pallet 21 is located at an original position, the first imaging system CT 22' is positioned adjacent to the bed pallet 21, and the second imaging system PET 23' is positioned away from the bed pallet 21. The bed pallet 21 is moved forward so that the patient is sent to the scanning plane 22 of the first imaging system CT 22'. Firstly, the patient is scanned by the first imaging system CT 22'. After the patient has been scanned by the first imaging system CT 22', the bed pallet 21 is moved back to the original position from a scanning position. Then, the bed 29 rotates by or through 180° by an automatic control device, so that the second imaging system PET 23' is positioned adjacent to the bed pallet 21 and the first imaging system CT 22' is positioned away from the bed pallet 21. The bed pallet 21 is moved forward so that the patient is sent to the scanning plane 23 of the second imaging system PET 23'. Then, the patient is scanned by the second imaging system PET 23'. After the patient has been scanned by the second imaging system PET 23', the bed pallet 21 is moved back to the original position. The scanning process is completed. Finally, the bed 29 reversely rotates by or through 180° by the automatic control device, so that the bed 29 is resumed to an original position thereof. In addition, the first imaging system CT 22' and the second imaging system PET 23' can maintain their respective full function abilities of clinic applications independently.

Although a few embodiments of the present invention have been shown and described, it would be appreciated by those skilled in the art that modifications changes may be made in these embodiments without departing from the principles and spirit of the invention, the scope of which is defined in the claims and their equivalents.

For example, in the above embodiments, a rotating device (the rotating base) is used so that the first imaging system and the second imaging system or the bed can be rotated, in order to assure that trajectories in which a patient is moved in different systems during scanning are consistent. However, the present application may use a moving manner, that is, a moving device movable on a guide, in stead of the rotating device. For example, the first imaging system and the second imaging system or the bed can be moved by a guide such as a rail and a moving device movable along the guide such as the rail, so as to assure that trajectories in which a patient, is moved in different systems during scanning are consistent. The moving manners include a translation manner and a composite motion manner. Therefore, the present invention can be achieved in a translation manner, a rotation manner, and a composite motion manner.

For example, in an embodiment, a moving device according to the present application can achieve a translation, a rotation, and a composition motion. For example, a rotating device is disposed on an apparatus that can perform a translation and a composition motion, so that a moving device is formed. When the first imaging system and the second imaging system or a bed (or a patient supporting device) are mounted on the moving device, the first imaging system and the second imaging system or the bed (or the patient supporting device) can perform a translation, a rotation, and a composite motion so as to assure that trajectories in which a patient is moved in different systems during scanning are uniform. For example, a device for a translation and a composition motion may be a table movable on a guide such as a rail, a carriage movable along a guide such as a runner or a rail, and the like.

For example, although the multimodality imaging system comprises only the first imaging system and the second imaging system in the above embodiments, it apparently may comprise a plurality of imaging systems such as 3, 4, 5, 6 or more imaging systems.

In addition, although the first imaging system and the second imaging system are disposed at an angle of 180° with respect to each other in the above embodiments, they may be disposed at any appropriate angle with respect to each other. For example, the first imaging system and the second imaging system may be disposed at an angle within a range of 70-180° with respect to each other.

Furthermore, although the first imaging system and the second imaging system and the bed rotate by or through an angle of 180° so that the first imaging system and the second imaging system are respectively positioned at a position to start to scan a patient in the above embodiments, the rotation angle is apparently not limited to the angle of 70-180°. The first imaging system and the second imaging system and the bed may rotate by or through any appropriate angle according to an angle at which the first imaging system and the second imaging system are disposed with respect to each other, so that the first imaging system and the second imaging system rotate in sequence to the position to start to scan a patient.

The invention claimed is:
1. A multimodality imaging system, comprising:
a first imaging system for forming a first image;
a second imaging system for forming a second image; and
a moving device on which the first imaging system and the second imaging system are fixed so that the first imaging system and the second imaging system are operable to be selectively moved to a scanning position,
wherein the moving device comprises a rotating device on which the first imaging system and the second imaging system are fixed so that the first imaging system and the second imaging system are operable to be selectively rotated to the scanning position; and
wherein the rotating device comprises:
a base disk on which the first imaging system and the second imaging system are fixed;

a base disk stand on which the base disk is rotatably supported; and a driving device adapted to rotate the base disk with respect to the base disk stand so as to rotate the first or second imaging system to the scanning position.

2. The multimodality imaging system according to claim 1, wherein the rotating device further comprises:

a detecting device for detecting a rotating angle of the base disk;

a braking device adapted to brake the rotating device according to the rotating angle of the base disk detected by the detecting device, so that the first or second imaging system is stopped at the scanning position.

3. The multimodality imaging system according to claim 1, wherein the rotating device further comprises:

an external gear type rotary bearing having an outer ring connected with the base disk, and an inner ring, the inner ring of the external gear type rotary bearing being fixed on the base disk stand;

a pinion meshing with an external gear on the outer ring of the external gear type rotary bearing; and a motor with a brake, the motor being connected with the pinion through a speed reducer, so that the motor is operable to rotate the base disk through the speed reducer, the pinion and the external gear on the outer ring of the external gear type rotary bearing.

4. The multimodality imaging system according to claim 3, further comprising:

a capacitive proximity switch support fixed at a position on an upper surface of the outer ring of the external gear type rotary bearing, a capacitive proximity switch fixed at a position on the capacitive proximity switch support, and an inclined metal block fixed at a position on the inner ring, wherein when the base disk rotates to a first angle, the capacitive proximity switch approaches the inclined metal block so that the capacitive proximity switch sends a control signal to control the motor to be decelerated; and when the base disk rotates to a second angle, the capacitive proximity switch sends control signal to control the motor to be braked and stopped.

5. The multimodality imaging system according to claim 3, further comprising:

a positioning device for selectively positioning the first imaging system and the second imaging system at the scanning position.

6. The multimodality imaging system according to claim 3, wherein the positioning device comprises:

a ball head plunger type positioning post sleeve part mounted at a position opposite to an edge of the base disk, and a stopping point recess formed in the edge of the base disk, wherein when the first or second imaging system is positioned at the scanning position, a ball of the ball head plunger type positioning post sleeve part is fitted in the stopping point recess formed in the edge of the base disk, so that the base disk is positioned with accuracy.

7. The multimodality imaging system according to claim 3, further comprising one of a bed, a movable patient table, a movable patient holder, and a movable patient supporting device for supporting a scanned patient.

8. An imaging method for forming images by using a first imaging system and a second imaging system, comprising:

moving a patient supporting device so as to send a patient to the first imaging system, and scanning the patient with the first imaging system;

moving the patient supporting device back to an original position thereof after the patient has been scanned with the first imaging system;

moving the patient supporting device to the second imaging system so as to send the patient to the second imaging system, and scanning the patient with the second imaging system; and moving the second imaging system to a scanning position before scanning the patient with the second imaging system, wherein:

moving the patient supporting device so as to send the patient to the first imaging system comprises moving a bed pallet of a bed forward so as to send the patient to the first imaging system;

moving the patient supporting device back to the original position thereof after the patient has been scanned with the first imaging system comprises moving the bed pallet of the bed back to an original position thereof after the patient after the patient has been scanned with the first imaging system;

moving the second imaging system to a scanning position comprises rotating the second imaging system to the scanning position, wherein rotating is achieved by a rotating device comprising a base disk on which the first imaging system and the second imaging system are fixed, a base disk stand on which the base disk is rotatably supported, and a driving device adapted to rotate the base disk with respect to the base disk stand so as to rotate the second imaging system to the scanning position; and moving the patient supporting device to the second imaging system so as to send the patient to the second imaging system comprises moving the bed pallet of the bed forward so as to send the patient to the second imaging system.

9. The imaging method according to claim 8, further comprising:

moving the bed pallet of the bed back to the original position thereof after the patient has been scanned with the second imaging system.

10. The imaging method according to claim 9, further comprising:

rotating the first imaging system to the scanning position.

* * * * *

UNITED STATES PATENT AND TRADEMARK OFFICE
CERTIFICATE OF CORRECTION

PATENT NO. : 7,941,203 B2
APPLICATION NO. : 11/903324
DATED : May 10, 2011
INVENTOR(S) : Quanlu Zheng et al.

Page 1 of 1

It is certified that error appears in the above-identified patent and that said Letters Patent is hereby corrected as shown below:

On the Title Page

Item (73) Assignee:
Delete "Neusolft"
Insert --Neusoft--

Signed and Sealed this
Thirteenth Day of May, 2014

Michelle K. Lee
*Deputy Director of the United States Patent and Trademark Office*